United States Patent [19]

Alexander

[11] Patent Number: 5,466,811
[45] Date of Patent: Nov. 14, 1995

[54] DIOXOLENYLMETHYL CARBAMATES PRO MOIETIES FOR AMINE DRUGS

[75] Inventor: Jose Alexander, Lawrence, Kans.

[73] Assignee: Merck & Co., Inc., Rahway, N.J.

[21] Appl. No.: 276,220

[22] Filed: Jul. 18, 1994

[51] Int. Cl.$^6$ .................. C07D 405/12; C07D 317/08; C07D 413/12; C07D 277/20
[52] U.S. Cl. .................. 546/283; 544/132; 544/148; 544/362; 544/363; 548/202; 548/465; 549/229
[58] Field of Search .................. 544/362, 363, 544/134, 148; 548/202, 465; 546/289; 549/229

[56] References Cited

U.S. PATENT DOCUMENTS 4,760,057  7/1988  Alexander ..................... 514/187

OTHER PUBLICATIONS

Alpegiani et al. Chem. Abst. 117:69628 (1992).
Miyauchi et al., Chem. Abst. 113:190997 (1990).
Sakamoto et al., Chem. Pharm Bull, vol. 33 (1985) 4870–4877.
Saari et al., J. Med. Chem. 1984, 27, 713–717.
Miyauchi et al. Chem. Pharm. Bull. 38(4), 1077–78 (1990).

*Primary Examiner*—Cecilia Tsang
*Attorney, Agent, or Firm*—Francis P. Bigley; Mark R. Daniel; Joseph F. DiPrima

[57] ABSTRACT

This invention relates to a the use of new oxodioxolenylmethyl carbamates to produce bioreversible neutral prodrugs from primary and secondary amines.

5 Claims, No Drawings

DIOXOLENYLMETHYL CARBAMATES PRO MOIETIES FOR AMINE DRUGS

BACKGROUND OF THE INVENTION

This invention relates to the use of dioxolenylmethyl carbamates which are useful in the production of neutral prodrugs from primary and secondary amines as well as the method of synthesis of such prodrugs. In particular, the novel prodrugs which are produced with a substituted 4-hydroxymethyl-2-oxo-1,3-dioxol-4-ene are presented.

The term "prodrug" denotes a derivative of a functional drug which derivative, when administered to a warm-blooded animal, "cleaves" in such a manner as to release the drug in its active form, at its target site or sites of activity. The enzymatic and/or chemical hydrolytic "cleavage" of the compound occurs in a manner such that the drug is released while the remaining "cleaved" promoiety remains non-toxic and is metabolized in such a manner that non-toxic, metabolic products are produced.

Pharmaceutically active compounds which are also known as drugs or pharmaceuticals or medicinals, which are amines or have an amine function therein can undergo protonation at physiological pH and are not always transported optimally through biological membranes in the body. For compounds which ionize, the rate of transport through biomembranes appears to be proportional to the concentration of undissociated molecules in solution and the lipid solubility.

It is often advantageous to perform derivatization of the polar amino groups to aid absorption, since this could make the compounds neutral, or more hydrophobic and hence more lipid soluble. Carbamylation confers such properties to amines since carbamates do not ionize at physiological pH. However, success with carbamate ester latentiation requires that it must be hydrolyzed to carbamic acid and the alcohol moiety after penetration through the biological barrier. This is especially true of carbamates of secondary amines, the rates of hydrolysis of which are $10^5$ to $10^9$ times slower than that of the corresponding primary amines. In this regard, there does not appear to be a carbamate ester specific hydrolytic enzyme in mammals. Though cholinesterase hydrolyze carbamates and become reversibly inhibited in the process, the rates are too slow for practical use. Hence, modified carbamates with an enzymically hydrolyzable ester function were designed as prodrugs for amines by Alexander (U.S. Pat. No. 4,760,057). Esterase catalyzed hydrolysis of the ester moiety triggers the regeneration of the parent amine from such derivatives as depicted below.

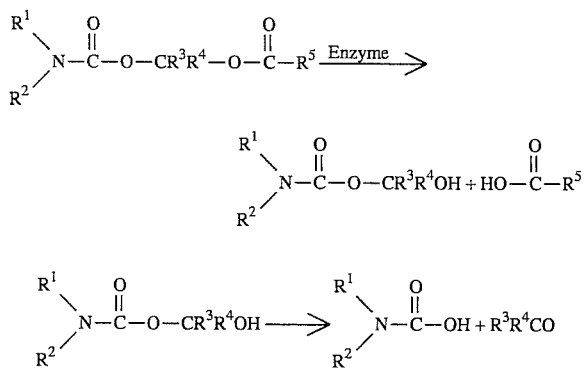

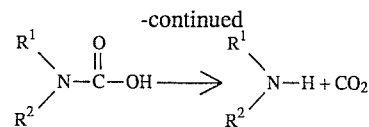

In the acyloxyalkyl carbamates described above, the acetal ester portion of the molecule is often derived from formaldehyde which is undesirable or from acetaldehyde. Use of the latter results in the introduction of a new chiral center, which may be useful or problematic. Application of the above invention to amino drugs which carry additional asymmetric centers elsewhere in the structure can result in the formation of a pair of diasteric isomeric prodrugs. The hydrolytic susceptibility of these diastereoisomers could be different and hence they could hydrolyze at widely different rates to regenerate the parent drug. Therefore, there is a need for a prodrug strategy that would confer bioreversibility and neutrality to the prodrug at physiological pH and at the same time would not introduce additional chiral centers in the prodrug, or generate undesirable side products.

2-Oxo-1,3-dioxolenylmethyl esters of carboxylic acid with the structure below, have been used as prodrugs for a variety of carboxyl-containing drugs. (Miyauchi, et al., Chem. Pharm. Bull. 1990, 38, 1077–1078; Saari, et al., J. Med. Chem., 1984, 27, 713–717.)

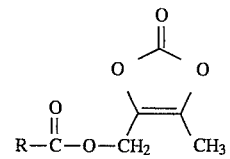

where R is a drug containing a carboxylic acid group.

5-Alkyl-2-oxo-1,3-dioxol-4-ylmethyl esters have been extensively investigated as prodrugs for carboxylic acid groups on B-lactam antibiotics of the penicillin, cephalosporin and thienamycin class of drugs. Lenampicillin (Ikeda, et al., J. Antibiotics, 1984, 32, 4316) is an orally active ampicillin prodrug using this prodrug group.

The 2-oxo-1,3-dioxolenylmethyl group has also been used as a prodrug moiety on the amino group of amino functional drugs as shown below (Sakamoto, et al., Chem. Pharm. Bull., 1985, 33, 4870–4877. )

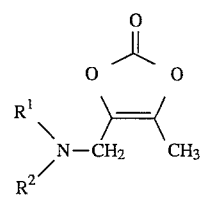

where $R^1R^2N$ is a drag containing an amino group. It has been used to alkylate the piperazino nitrogen in norfloxacin (Sakamoto, et al, Chem. Pharm. Bull., 1985, 33, 4870). The alkylated nofloxacin regenerated the parent drug on oral administration to rats.

The direct alkylation of the amino group with the oxo-dioxolenylmethyl functionality as above gives a substituted amine that can undergo protonation and is still ionizable. That is, the hydrophilic nature of the amino group or solubility property of the prodrug is not significantly changed by this type of modification.

U.S. Pat. No. 4,760,057, discloses alkalylated compounds prepared by a two-step process comprising the steps of treating a primary or secondary amine with an alpha-haloalkyl halo-formate to give an alpha-haloalkyl carbamate followed by displacement of the halogen with an acyloxy group by treatment with a metal salt of the carboxylic acid; the metal used could be alkali, alkaline earth, or silver, mercury, and the like.

However, there are instances where the application of the method could result in poor yields as a result of side reactions. For example, silver salts could interact with a free thiol function or mercury salts could give rise to mercuration of highly activated aromatic rings and double bonds. Therefore, there exists a need for a prodrug forming mechanism that will result in primary or secondary amines which are less susceptible to ionization at physiological pH and are free from the side reactions already discussed.

Accordingly, this invention provides novel dioxolenylmethyl carbonate derivatives which are useful as starting materials for novel one-step synthesis of bioreversible prodrug moieties for drugs or medicaments having primary or secondary amine functions thereon which when administered to warm-blooded animals are characterized as being more readily bioavailable, less irritating to topical and gastric mucosal membranes and more permeable through topical membranes, e.g., ophthalmic membrane or skin, than are the parent drugs from which they are derived.

The prodrug of this invention form from conventional primary and secondary amine compounds which, following administration, will "cleave" in such a manner as to enable the original parent moiety to be released at its therapeutic site or sites of activity and to further permit the cleaved moiety, unassociated with the parent moiety, to be metabolized in a non-toxic fashion.

This invention also provides prodrugs of medicaments or drugs having primary or secondary amine functions thereon to provide increased biomembrane transport such that the drug is more bioavailable from the GI tract, the rectum, the skin and the eye of the human body.

A further advantage of this invention is to provide prodrug compounds which utilize hydrolytic enzymes to generate the parent amine-type drug from the prodrug or carbamate protecting group. An additional advantage of this invention is that it provides prodrugs of amines wherein the reactive function is remote from the carbamate carbonyl and thus enzymatic hydrolysis leads to the generation of carbamic acid which will undergo fast decarboxylation releasing the amine parent drug.

In the instant invention, the problems observed with the previously reported systems have been overcome. In the instant invention, a primary or secondary amino functional drug is convened to produce the prodrug moiety shown below:

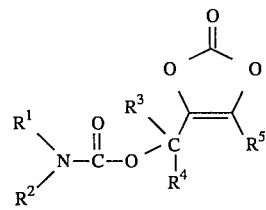

An oxodoxolenyl methyl carbamate prodrug results by carbamylation of the amino group with a substituted 4-hydroxymethyl-2-oxo-1,3-dioxol-4-ene to produce the prodrug moiety.

Carbamylation of the amino group provides the following advantages for the resulting prodrug:
(a) carbamylated amines do not ionize and hence are more compatible with organic and lipoidal systems;
(b) the modification is applicable to primary and secondary amines essentially irrespective of basicity;
(c) there is potential for chemical selectivity in the presence of competing functionalities such as hydroxyl;
(d) they are chemically stable;
(e) when $R^3$ and $R^4$ are the same, this promoiety produces a prodrug with no additional chiral centers; and
(f) enzyme catalyzed ring opening of the oxodioxolene ring triggers the regeneration of the parent primary or secondary amine as shown below:

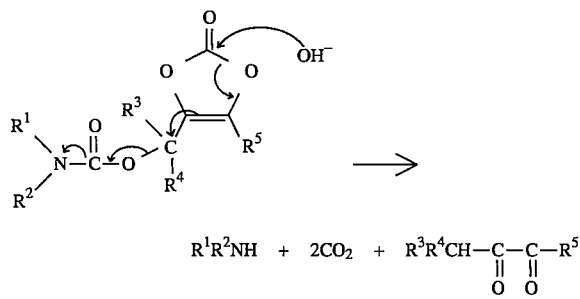

The novel method of this invention provides for the production of a bioreversible prodrug from primary or secondary amines wherein the ionizability of the resultant prodrug, under physiologic pH, is masked such that lipid solubility is increased, and hydrophilic properties are reduced. Further, the novel process of this invention, results in high yield of the prodrug without the use of reagents that promote side reactions.

SUMMARY OF THE INVENTION

In accordance with this invention, there is provided novel prodrugs which are oxodioxolenylmethyl carbamate derivatives of Formula I:

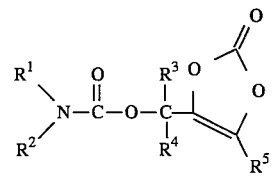

Formula I where

is a primary or secondary amine, and $R^1$ and $R^2$ are the same or different or may be combined to form a cyclic secondary amine;

$R^3$ is hydrogen, straight or branched chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy;

R4 is hydrogen, straight or branchanged chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy;

R5 is hydrogen, straight or branchanged chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy.

For the purposes of this specification, the term "prodrug" denotes a derivative of a known and proven primary or secondary amino functional drug (e.g. timolol, methyldopa, thiabendazole, etc.) which derivative, when administered to a warm-blooded animal, "cleaves" in such a manner as to release the proven drug form at its target site or sites of activity. The enzymatic and/or chemical hydrolytic "cleavage" of the compounds of the instant invention occurs in a manner such that the proven drug form is released while the remaining "cleaved" moiety remains non-toxic and is metabolized in such a manner that non-toxic, metabolic products are produced.

DETAILED DESCRIPTION OF THE INVENTION

This invention, provides novel prodrugs which are oxodioxolenylmethyl carbamate derivatives of Formula I:

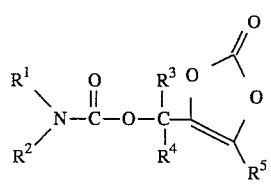

Formula I where

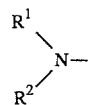

is a primary or secondary amine, and $R^1$ and $R^2$ are the same or different or may be combined to form a cyclic secondary amine;

$R^3$ is hydrogen, straight or branched chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy;

R4 is hydrogen, straight or branchanged chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy;

R5 is hydrogen, straight or branchanged chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy.

The invention further concerns preparation and use of novel oxodioxolenylmethyl carbonate derivatives that are used as a starting material in a novel one-step synthesis of bioreversible prodrug moieties for drugs or medicaments having primary or secondary amine functions which increases the bioavailability of said prodrug or medicament in the gastrointestinal tract, rectum, skin and eye of the patient (animal and human). The novel (oxodioxolenylmethyl)carbonate derivatives of the invention are represented by the following Formula II:

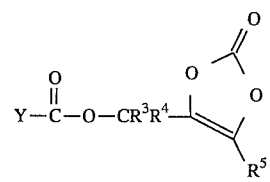

Formula II where $R^3$ is hydrogen, straight or branched chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy;

R4 is hydrogen, straight or branchanged chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy;

R5 is hydrogen, straight or branchanged chain $C_1$ to $C_6$ alkyl, straight or branched chain $C_1$ to $C_6$ alkenyl, phenyl, substituted phenyl wherein the substitutents are fluoro, chloro, bromo, iodo, nitro, C1 to C6 carboxyalkyl, or C1 to C6 alkyloxy;

where Y is halo, a tertiary amine salt, p-nitro phenoxy, dinitrophenoxy, pentachlorophenoxy, or pentafluorophenoxy, pyridinium ion or 4-dimethyl amino pyridinium ion.

In the present invention, a primary or secondary amino functional drug is converted to an oxodioxolenylmethyl carbamate prodrug by carbamylation of the amino group with a derivatized 4-hydroxymethyl-2-oxo- 1,3-dioxol-4-ene as shown:

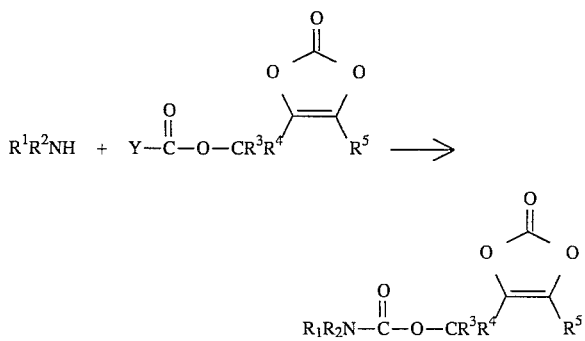

where Y is halo, preferably chloro or amine conjugated such as pyridinium ion or a good leaving group such as p-nitro phenoxy, dinitrophenoxy, pentachlorophenoxy, pentafluorophenoxy and the like.

Various active agents provide beneficial effects when administered to patients. Representative drugs, pharmaceuticals or medicaments which can be used and which contain primary or secondary amine functions thereon are listed below. One skilled in the art will realize that the list below is not exclusive and the invention is applicable to other primary and secondary amino functional drugs as well.

Those drugs, pharmaceuticals or medicaments containing primary and secondary amines such as timolol: acebutalol, albuterol, alprenolol, atenolol, bucindolol, bunolol, butopamine, butoxamine, carbuterol, cartelolol, colterol, deterenol, dexpropranolol, diacetolol, dobutamine, exaprolol, fenoterol, fenyripol, labotolol, levobunolol, metolol, metaproterenol, metoprolol, nadolol, exprenolol, pamatolol, penbutalol, pindolol, pirbuterol, practolol, prenalterol, primidolol, prizidilol, procaterol, propranolol, quinterenol, rimiterol, ritodrine, sotolol, soterenol, sulfinolol, sulfonterol, suloctidil, tazolol, terbutaline, tiprenolol, tipropidil, tolamolol, thiabendazole, albendazole, albutoin, alinidine, alizapride, amiloride, aminorex, aprinocid, cambendazole, cimetidine, clonidine, cyclobendazole, etintidine, fenbendazole, fenmetazole, flubendazole, fludorex, lobendazole, mebendazole, metazoline, nocodazole, oxfendazole, oxibendazole, oxmetidine, parbendazole, ranitidine, tetrahydrazoline, tiamenidine, tinazoline, tiotidine, tolazoline, tramazoline, xylometazoline, dimethoxyphenethylamine: adrenelone, aletamine, amidephrine, amphetamine, aspartame, bamethan, betahistine, clorprenaline, chlortermine, dopamine, etryptamine, fenfluramine, norepinephrine, tocainide, etc.

Other drugs are acyclovir, enviroxime, nifedipine, nimodipine, triamterene, vidarabine, methyldopa, epinephrine and those structurally similar to norfloxacin such as pipemidic acid, 1-ethyl- 6-fluoro- 1,4-dihydro-4-oxo-7-(1-piperazinyl)-1,8-naphthyridine- 3- carboxylic acid and 1-cyclopropyl-6-fluoro-1,4-dihydro-4-oxo- 7-( 1-piperezinyl)-3-quinolinecarboxylic acid.

The prodrug compounds of Formula I can be used to treat any condition for which the parent drug, medicament or pharmaceutical is useful. For example, if timolol is the parent drug of choice, the prodrug can be used for any condition or treatment for which timolol would be administered. Thus, the prodrug compounds of this invention may be administered orally, topically, parentally, by inhalation spray or rectally in dosage unit formulations containing conventional, non-toxic pharmaceutically acceptable carders, adjuvants and vehicles.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions untended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present. The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectibles.

The compounds of the above formula may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug, for example, cocoa butter and polyethylene glycols.

For topical use, creams, ointments, jellies, solutions, suspensions or the like containing the prodrugs are employed according to methods recognized in the art. Naturally, the therapeutic dosage range for the compounds of the invention will vary with the size and needs of the patient and the particular pain or disease symptom being treated. However, generally speaking, the following dosage guidelines will suffice. Orally, the therapeutic dose required for a compound of the invention will generally, on a molecular basis, mimic that for the parent primary or secondary amine drug. On a topical basis, application of from about 0.01% to about 2.5% concentration of a compound of the invention (in a suitable topical carder material) to the affected site should suffice.

The amount of active ingredient that may be combined with the carrier materials to produce a single dosage form will vary depending upon the host treated and the particular mode of administration. For example, a formulation intended for the oral administration of humans may contain from about 5 mg to about 5 gm of active agent compounded with an appropriate and convenient amount of carrier material which may vary from about 5 to about 95 percent of the total composition. Other dosage forms such as ophthalmic dosage forms contain less active ingredient such as for example from about 0.1 mg to about 5 mg. Dosage unit forms will generally contain between from about 0.1 mg to about 1 g of active ingredient. It will be understood, however, that the specific dose level for any particular patient will depend upon a variety of factors including the activity of the specific compound employed, the age, body weight, general heath, sex, diet, time of administration, route of administration, rate of excretion, drug combination and the severity of the particular disease undergoing therapy.

As an illustration of this invention but not as a limitation thereof, the following examples embodying the invention are presented.

EXAMPLE 1

Preparation of 4,5-dimethyl-1,3-dioxolene-2-one

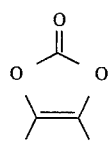

Triphosgene (60 g) was added to an ice cold solution of 3-hydroxy-2-butanone (44 g) in ethylene dichloride (500 mL). N,N-dimethylaniline (72.7 g) diluted with an equal volume of ethylene dichloride was added dropwise to the reaction mixture. The temperature was maintained below 8° C. After the addition of the dimethylaniline was complete, the reaction mixture was allowed to stir at ice bath temperature for 15 minutes. The ice bath was removed, the mixture was allowed to warm up to room temperature and stirred for 2 hours. The reaction mixture was cooled to 5° C. and washed with ice cold 3N hydrochloric acid, ice cold water, and brine. The ethylene dichloride solution was dried over sodium sulfate and concentrated to about 250 mL. It was refluxed for 3 hours and then the solvent was evaporated off to obtain a residue that weighed 67.92 g. The crude product was heated at 170° C. with continuous argon flushing for 2 hours. The resulting dark product was boiled in benzene with charcoal. The charcoal was filtered off and the flitrate concentrated to about 100 mL. Hexane was added to the residue and placed in an ice bath for 20 minutes. The crystals formed were filtered and washed with ice cold hexane to furnish 41.86 g of colorless solid. The solid was recrystallized from hexane (40.1 g, 70% yield); mp 80°–81° C., $^1$H NMR (CDCl$_3$) δ2.03; IR (KBr) 1800, 1735, 1256, 1192, 1019, 769 cm$^{-1}$.

EXAMPLE 2

Preparation of 4-bromomethyl-5-methyl-1,3-dioxolene-2-one

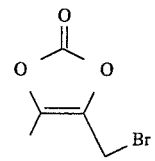

4,5-Dimethyl-1,3-dioxolene-2-one (11.4 g) was mixed with N-bromosuccinimide (19.6 g) and 2,2-azobis(2-methylpropionitrile) (0.5 g) in freshly distilled carbon tetrachloride (350 mL) and refluxed for 6 hours under an argon atmosphere. The reaction mixture was cooled in an ice bath after reflux and the precipitate formed was filtered off. The tiltrate was washed with water and brine, and dried over sodium sulfate. The solvent was evaporated to yield a yellow oil (20.54 g) which was distilled to obtain the pure monobromomethyl compound as a light yellow oil (11.86 g, 54%), bp 93° C. at 0.45 mm; $^1$H NMR (CDCl$_3$) δ2.15 (s, 3H), 4.21 (S, 2H); IR (film) 1820, 1728, 1392, 1201, 1236, 768 cm$^{-1}$.

See F. Sakamoto, S. Ikeda, G. Tsukamoto, Chem. Pharm. Bull., 32, 2241–2248 (1984) JP 8763983 A2; JP 6253983, Date 870309 (CA:108(7)56100y); JP 83152879 A2; JP 58152879 Date: 830910 (CA:100 (15) 121042 g)

EXAMPLE 3

Preparation of 4-formyloxymethyl-5-methyl-1,3-dioxolene-2-one

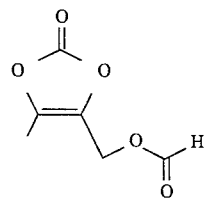

To a solution of trimethylamine (36 g) and formic acid (11.4 g) in acetonitrile (250 mL) the above bromomethyldioxolenone (11.8 g) was added and stirred at room temperature for 1 hour. The acetonitrile was evaporated off, the residue was dissolved in water and extracted with ethyl acetate. The organic extract was washed with water and brine and dried over sodium sulfate. Evaporation of solvent gave a light brown liquid (7.61 g, 82%); $^1$H NMR (CDCl$_3$) δ2.2 (S, 3H), 4.94 (s, 2H), 8.09 (S,1H).

See M. Alpegiani, F. Zarini, E. Perrone, Synthetic Communications, 22, 1277–1282, (1992).

EXAMPLE 4

Preparation of 4-hydroxymethyl-5-methyl-1,3-dioxolene- 2-one

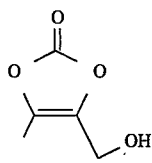

The above formuyloxymethyldioxolenone (7.6 g) was dissolved in methanol (100 mL) and 0.3 mL of 36% hydrochloric acid was added. After stirring one hour at room temperature the methanol was evaporated off. The residue was applied to a column of silica gel (100 g) and eluted with ethyl acetate. The pure 4-hydroxymethyl- 5-methyl-1,3-dioxolen-2-one (5.59 g, 93%) was obtained as a colorless oil; $^1$H NMR (CDCl$_3$) δ2.14 (s, 3H), 3.35 (bs, 1H), 4.40 (s, 2H); IR (film), 3428, 1825, 1735, 1222, 1180, 1006 cm$^{-1}$.

See M. Alpegiani, F. Zarini, E. Perrone, Synthetic Communications, 22, 1277–1282, (1992).

EXAMPLE 5

Preparation of (5-methyl-1,3-dioxolene-2-one-4-yl)-methyl p-nitrophenyl carbonate

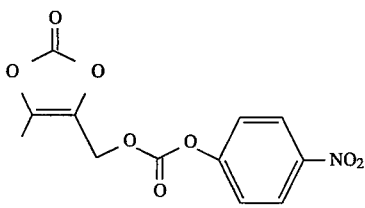

4-Hydroxymethyl-5-methyl-1,3-doxolene-2-one (5.59 g) and pyridine (3.74 g) were dissolved in 50 mL of chloroform and cooled in an ice bath. 4-Nitrophenylchloroformate (9.46 g) dissolvedin chloroform (50 mL) was added dropwise to the above solution. The mixture was stirred for 16 hours at room temperature. The reaction mixture was cooled in ice and washed with ice cold 1% sodium hydroxide, 1N hydrochloric acid, water and brine and dried over sodium sulfate. Evaporation of the organic layer resulted in 11.2 g of crude product, which was crystallized from chloroform/hexane. The crystals formed were filtered and washed with ice cold hexane/chloroform (1:1), to obtain the pure 4-nitrophenyl carbonate (9.11 g, 81%); mp 116°–117°; $^1$H NMR (CDCl$_3$) δ2.23 (s, 3H), 5.05 (s,2H), 7.41 (d, 2H), 8.3 (s, 2H); $^{13}$C NMR (CDCl$_3$), δ9.43, 58.07, 121.69, 121.35, 132.15, 141.42, 145.57, 151.66, 152.19, 155.05; IR (KBr) 1779, 1811, 1525, 1247, 1221, 1207 cm$^{-1}$.

EXAMPLE 6

Preparation of N-(5-methyl-2-oxo-1,3-dioxololen-4-yl)-methylcarbamoyl norfloxacin

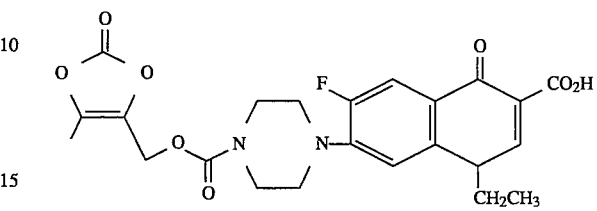

A mixture of norfloxacin (0.26 g) and p-nitrophenyl 5-methyl-2-oxodioxolenylmethyl carbonate (0.28 g) in dimethylformamide (6 mL) was stirred at room temperature for 48 hours. The reaction mixture was diluted with water to about 25 mL, filtered, the solid was washed with water and dried. The product weighed 0.3 g; 1H NMR (DMSO-d$_6$) δ1.41 (t, 3H), 2.18 (s, 3H), 3.37 (br, 4H), 3.61 (br, 4H), 4.59 (q, 2H), 4.98 (s, 2H), 7.21 (d, 1H), 7.94 (d, 1H), 8.896 (s,1H). 1H).

EXAMPLE 7

Preparation of 5'-methyl-2'-oxo- 1',3'-dioxol-4'-enyl-4'-methylcarbamoyl-3,4-dimethoxyphenethylamine To a solution of 4-Hydroxymethyl-5-methyl-2-oxo- 1,3-dioxol-4-ene (1.3 g) in ice cold tetrahydrofuran (25 mL) triphosgene (1.05 g) was added. A solution of 4-dimethylaminopyridine (1.28 g) was added dropwise to the reaction mixture during 15 minutes and stirred at ice bath temperature for 2 hours under nitrogen atmosphere. The solution of the chloroformate formed was filtered to remove the precipitated 4-dimethylamknopyridine hydrochloride and transferred through a teflon tube by nitrogen pressure to a solution of 3,4-dimethoxyphenethylamine (1.81 g) and 4-dimethylaminopyridine (1.22 g) in chloroform (50 mL) maintained at ice bath temperature. After stirring the reaction mixture for one hour at ice bath temperature, the cooling bath was removed and allowed to warm up to room temperature for an hour. The tetrahydrofuran and chloroform were evaporated off, the residue was taken in ethyl acetate and washed with 1N hydrochloric acid and water. The ethyl acetate layer was dried over sodium sulfate and evaporated. The residue which weighed 1.19 g was purified by preparative TLC on silica gel plates to obtain 0.26 g of the pure oxodioxolenylmethylcarbamate, as a colorless thick oil. $^1$H NMR (CDCl$_3$) δ2.17 (3H, s), 2.76 (2H, t), 3.42 (2H, m), 3.86 (6H, s), 4.79 (2H, s) 4.97 (1H, br) and 6.7 to 6.83 (eH, m). $^{13}$C NMR (CDCl$_3$) δ9.18, 35.39, 42.25, 53.95, 55.71, 55.76, 111.19, 111.71, 120.55, 130.75, 133.91, 139.71, 147.60, 148.87, 152.15, 155.26,; MS m/e 337 (M$^+$) 207, 165, 151, 130.

EXAMPLE 8

Preparation of {3(R)-{2-[1-5'-methyl-2'oxo-1',3'-dioxol-4'-enyl-4'-methylcarbamoyl)-piperidine-4-yl]-ethyl}2-piperidone-1}-acetyl-3(R)-methyl-β-alanine A mixture of [3(R)-2-piperidine-4-yl-ethyl] 2-piperidone-1]-acetyl-3(R)-methyl-β-alanine and 5 methyl-2-oxo-1,3- dioxol-4-enylmethyl p-nitrophenyl carbonate (290 mg, 2 mmole) in dimethylformamide (10 mL) was stirred at room temperature. A solution was obtained within about one hour. After 20 hour, the reaction mixture was diluted with water to about 35 mL and extracted with ethyl acetate. The organic layer was washed with water and brine and dried over sodium sulfate. Evaporation of solvent gave a residue that weighed 1.3 g. It was purified by chromatography over Sephade ® LH20 (50 g). Elution with chloroform gave the pure dioxolenylmethylcarbamate as a resinous solid (954 mg). $^1$H NMR (CDCl$_3$) δ0.9–2.1 (13H, m), 1.27 (3H, d), 2.18 (3H, s), 2.35 (1H, m), 2.52 (2H, d), 2.75 (2H, m), 3.42 (2H, m) 3.97 (2H, q), 4.08 (2H, m), 4.32 (1H, m), 4.83 (2H, s), 6.35 (1H, br), 7.01 (1H, d) $^{13}$C NMR (CDCl$_3$) δ9.33, 19.87 μ21,38, 25.95, 28.73, 31.68, 31.93, 33.44, 35.79, 39.71, 41.31, 41.99, 44.27, 49.83, 51.79, 54.55, 134.12, 139.69, 152.35, 154.31, 168.14, 174.07; HRFAMBS, m/e 508.2313, calcd. for $X_{24}H_{34}N_3O_9$ (M-1), 508.2295.

EXAMPLE 9

Hydrolysis in Rat Plasma

The process of hydrolysis of the dioxolenylmethyl carbamate of 3,4-dimethoxyphenethylamine was studied by measuring the formation of dimethoxyphenethylamine at 37° C. in neat rat plasma. The reaction was initiated by adding a dimethyl sulfoxide (DMSO) solution of the carbamate to the reaction medium pre-equilibrated at 37° C. in a thermostated water bath. The initial concentrations of the carbamate in rat plasma was $4.3\times10^{-3}$M and the concentration of DMSO was 10%. Samples (100 μL of acetonitrile, vortex mixed for 30 seconds to precipitate the plasma proteins, and centrifuged at 10,000 X g for 5 minutes. The supernatants were injected directly and analyxed by HPLC. The HPLC column used was a 10 cm spheri-5 RP-18 column combined with a similar 3 cm guard column. The mobile phase used for the analysis of dimethoxyphenethylamine was 30% v/v of acetonitrile in water containing 0.5 mL/L of 85% phosphoric acid and 0.5 mL/L of triethylamine at a flow rate of 2 mL per minute. The concentration was measured at 280 nm using a variable wave length UV detector. The retention time of dimethoxyphenethylamine under these conditions was 5.8 minutes. The half-life for the hydrolysis of the dioxolenylmethyl carbamate to the product, dimethoxyphenethylamine, in rat plasma at 37° C. was 11 minutes.

What is claimed is:

1. A prodrug moiety which comprises a derivatized 4-hydroxymethyl-2-oxo-1,3-dioxol-4-ene of Formula II:

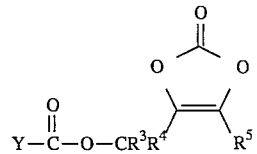

Formula II where

R$^3$ is hydrogen, straight or branched chain C$_1$ to C$_6$ alkyl, straight or branched chain C$_1$ to C$_6$ alkenyl, phenyl, substituted phenyl wherein the substitutents are fluoro, chloro, bromo, iodo, nitro, C1 to C6 carboxyalkyl, or C1 to C6 alkyloxy;

R4 is hydrogen, straight or branchanged chain C$_1$ to C$_6$ alkyl, straight or branched chain C$_1$ to C$_6$ alkenyl, phenyl, substituted phenyl wherein the substitutents are fluoro, chloro, bromo, iodo, nitro, C1 to C6 carboxyalkyl, or C1 to C6 alkyloxy;

R5 is hydrogen, straight or branchanged chain C$_1$ to C$_6$ alkyl, straight or branched chain C$_1$ to C$_6$ alkenyl, phenyl, substituted phenyl wherein the substitutents are fluoro, chloro, bromo, iodo, nitro, C1 to C6 carboxyalkyl, or C1 to C6 alkyloxy; and where Y is halo, p-nitro phenoxy, dinitrophenoxy, pentachlorophenoxy, or pentafluorophenoxy, pyridinium ion or 4-dimethyl amino pyridinium ion.

2. The prodrug moiety of claim 1, where Y is halo.

3. The prodrug moiety of claim 1, where Y is chloro or bromo.

4. The prodrug moiety of claim 1 where Y is p-nitrophenoxy.

5. The prodrug moiety of claim 1 where Y is pyridinium cation, 4-dimethylamino pyridinium cation.

* * * * *